(12) United States Patent
Zupancic et al.

(10) Patent No.: US 7,875,641 B2
(45) Date of Patent: Jan. 25, 2011

(54) SESQUIHYDRATE HYDROCHLORIDE SALT OF IRBESARTAN

(75) Inventors: Silvo Zupancic, Novo mesto (SI); Matej Smrkolj, Izlake (SI); Renata Jaske, Smarjeske Toplice (SI)

(73) Assignee: KRKA Tovarna Zdravil, D.D., Novo Mesto, Novo Mesto (SI)

( * ) Notice: Subject to any disclaimer, the term of this patent is extended or adjusted under 35 U.S.C. 154(b) by 936 days.

(21) Appl. No.: 11/658,632

(22) PCT Filed: Jul. 29, 2005

(86) PCT No.: PCT/SI2005/000023

§ 371 (c)(1),
(2), (4) Date: Jan. 26, 2007

(87) PCT Pub. No.: WO2006/011859

PCT Pub. Date: Feb. 2, 2006

(65) Prior Publication Data

US 2008/0306128 A1    Dec. 11, 2008

(30) Foreign Application Priority Data

Jul. 29, 2004  (SI) ............................ P-200400220
Oct. 22, 2004  (SI) ............................ P-200400292

(51) Int. Cl.
*A61K 31/41*   (2006.01)
*C07D 257/04*  (2006.01)

(52) U.S. Cl. ...................................... 514/381; 548/250
(58) Field of Classification Search ................. 514/381; 548/250
See application file for complete search history.

(56) References Cited

U.S. PATENT DOCUMENTS

| | | |
|---|---|---|
| 5,541,209 A | 7/1996 | Spinale |
| 5,629,331 A | 5/1997 | Caron et al. |
| 6,800,761 B1 | 10/2004 | Franc et al. |

FOREIGN PATENT DOCUMENTS

| | | |
|---|---|---|
| EP | 0 454051 | 10/1991 |
| EP | 0 708 103 | 4/1996 |
| WO | WO 99/67236 | 12/1999 |
| WO | WO 03/050110 | 6/2003 |

OTHER PUBLICATIONS

Morissette et al. (Advanced Drug Delivery Reviews, vol. 56, pp. 275-300; 2004).*
Vippagunta et al. (Advanced Drug Delivery Reviews, vol. 48, Abstract; 2001).*
Bauer, Michel et al., NMR study of desmotropy in Irbesartan, a tetrazole-containing pharmaceutical compound, *J. chem.. Soc., Perkin Trans.* 2, 1998 p. 475-481.
Bocskei, Zsolt et al., Irbesartan Crystal Form B, *Acta Cryst.* (1998) C54, 808-810.
Bernhart, Claude A., et al., A New Series of Imidazolones: Highly Specific and Potent Nonpeptide $AT_1$ Angiotensin II Receptor Antagonists, *J. Med. Chem.* 1993, 36, 3371-3380.

* cited by examiner

*Primary Examiner*—Phyllis G. Spivack
*Assistant Examiner*—Nelson C Blakely, III
(74) *Attorney, Agent, or Firm*—Cohen Pontani Lieberman & Pavane LLP

(57) ABSTRACT

The present invention relates to sesquihydrate hydrochloride salt of irbesartan and pharmaceutical compositions comprising the same.

8 Claims, 3 Drawing Sheets

SESQUIHYDRATE HYDROCHLORIDE SALT OF IRBESARTAN

PRIORITY CLAIM

This is a U.S. national stage of application No. PCT/SI2005/000023, filed on Jul. 29, 2005. Priority is claimed on the following application(s): Country: Slovenia, Application No.: P-200400220, Filed: Jul. 29, 2004 and Application No. P-200400292, filed Oct. 22, 2004, the content of which is incorporated here by reference.

TECHNICAL FIELD

The present invention belongs to the field of organic chemistry and relates to new forms of 2-butyl-1-[2'-(1H-tetrazol-5-yl)bifenyl-4-yl-methyl]spiro[2-imidazoline-4.1'-cyclopentane]-5-one (in the continuation irbesartan) and to a process for the preparation thereof.

TECHNICAL PROBLEM

Irbesartan or 2-butyl-1-[2'-(1H-tetrazol-5-yl)bifenyl-4-yl-methyl]spiro[2-imidazoline-4.1'-cyclopentane]-5-one is an antagonist of angiotensin-II receptors or so-called receptors AT-1 and AT-2. By binding irbesartan instead of angiotensine II to these receptors, the vasoconstrictive action of angiotensin-II is prevented and therefore irbesartan acts as an antihypertensic. The compound prepared according to the state of the art in the form of a polymorph form A crystallizes in the form of stable and non-hygroscopic needles, which can be stored and incorporated into pharmaceutical formulations without any decomposition. However, they have the disadvantage that much caution is necessary when handling them in the preparation of pharmaceutical formulations because the form A of irbesartan is very electrostatic and readily accumulates on the walls of the vessels e.g. on sieves, in tabletting machines or mills.

The problem of electrostaticity is partly solved in WO 99/67236 or EP 1089994, wherein irbesartan of a special morphological form of crystals with modified properties is claimed. The ratio between the length and the width of irbesartan crystals of this morphological crystal form is between 1:1 and 10:1, preferably between 1:1 and 5:1 and its capacitivity is from 0 to −10 nC/g. The process for its preparation is characterized in that a suspension of crystals of form A is subjected to temperature oscillation or mechanic shearing, which in pharmaceutical industry represents a complicated, not easily controllable and not easily repeatable process.

Therefore there still exists the need for an improved process for the preparation of irbesartan with a smaller electrostaticity, whereby the above-mentioned disadvantages would be avoided and irbesartan having both purity and electrostaticity suitable for the preparation of pharmaceutical formulations on an industrial scale would be prepared.

These problems are solved by the present invention.

PRIOR ART

The synthesis of irbesartan is described in EP 0 454 511 B1. In EP 0 708 103 as well as in the article Bernhart, C. A; Perreaut, P. M., Ferrari, B. P. et al.: >>A new series of imidazoloxies: Highly specific and potent nonpeptide AT1 angiotensin II receptor antagonists<<, J. Med. Chem. 1993, 36, pp. 3371-80 it is stated that form A is prepared according to the process of EP 0 454 511 B1.

In EP 0 708 103 a process for the preparation of both crystal forms A and B of irbesartan, the crystal form B and pharmaceutical compositions containing the same are claimed. It is stated in the prior that the crystals of form A of the basic patent or article are acicular, non-hygroscopic and do not decompose. There are, however, mentioned great problems because they are highly electrostatic and hence accumulate very readily on walls of vessels and apparatus. If for the crystallization of irbesartan a solvent containing less than 10% of water is used, the form A is formed, if the solvent system contains more than 10% of water, the form B is formed. For the latter it was found that it demonstrates a lesser electrostaticity and the same stability as the form A and does not convert to the former. It is stated that the pH may not be lower than 2-3, otherwise irbesartan B does not precipitate. The form B is a tautomeric form of irbesartan, wherein the hydrogen atom is situated in the tetrazole ring on N2 atom. This was also confirmed in the article in Acta Cryst., 1998, C54, p. 808-810, where the X-ray structure was published.

In the article J. Chem. Soc., Perkin Trans. 2, 1998, pp. 475-481 it is stated that a suspension of irbesartan form A in an aqueous HCl solution at pH=2 converts to the form B after 36 hours at room temperature. The form A converts to the form B in water at a pH from 2 to 8. At a higher pH a dissolution of irbesartan and the formation of a salt occur. An opposite process, i.e. the conversion of form B to form A does not occur.

In WO 99/67236 or EP 1089994 there is claimed irbesartan of a special morphological form of crystals with modified properties, wherein the ratio between the length and the width of crystals is between 1:1 and 10:1, preferably between 1:1 and 5:1 and its capacitivity is from 0 to −10 nC/g of irbesartan. In addition to the special morphological form of crystals there is also claimed a method for its preparation and pharmaceutical compositions containing the same. The method is characterized in that a suspension of crystals of form A is subjected to temperature oscillation or mechanic shearing, which represents a complicated and not easily repeatable process in pharmaceutical industry. Hereby a conversion to a special morphological form of crystals having the above-mentioned modified properties occurs.

WO 03/050110 discloses the preparation of a new amorphous form of irbesartan and a process for its preparation including dissolving crystal forms A or B in a solvent mixture consisting of halogenated alkanes and alcohols at room temperature, followed by evaporation of the solvents to a dry amorphous irbesartan.

U.S. Pat. No. 5,541,209 discloses the use of irbesartan for the treatment and prevention of cardiac arrhythmia and the preparation of sodium and potassium salt of irbesartan from alkaline solutions. As possible pharmaceutically acceptable salts, in addition to alkaline salts such as sodium or potassium salt there are also mentioned amine salts such as trometramol salt, aminoacid salts such as arginine and lysine salts and addition salts with acids such as hydrochloride, hydrobromide, sulfate, hydrogensulfate, dihydrogenphosphate, methanesulfonate, methylsulfate, maleate, fumarate and naphthalen-2-sulfonate.

SUMMARY OF THE INVENTION

Figure 1:
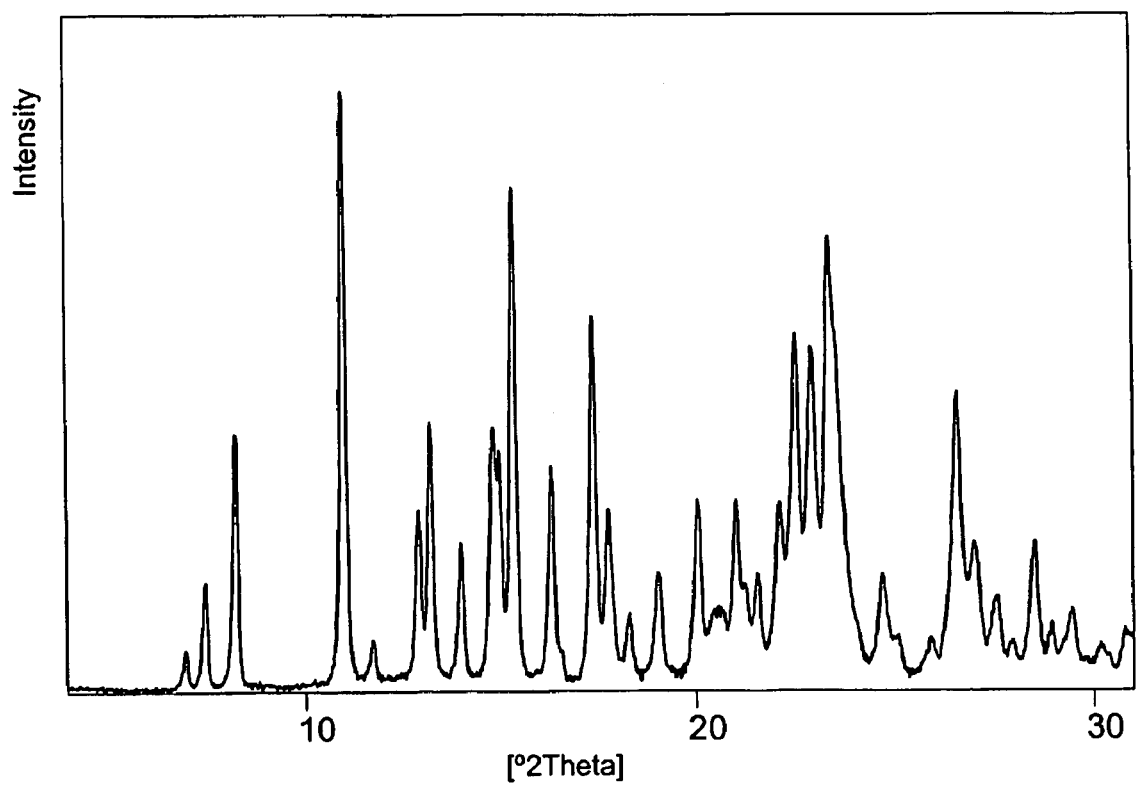
FIG. 1 represents X-ray powder diffractogram of sesquihydrate hydrochloride salt of irbesartan.
Figure 2:
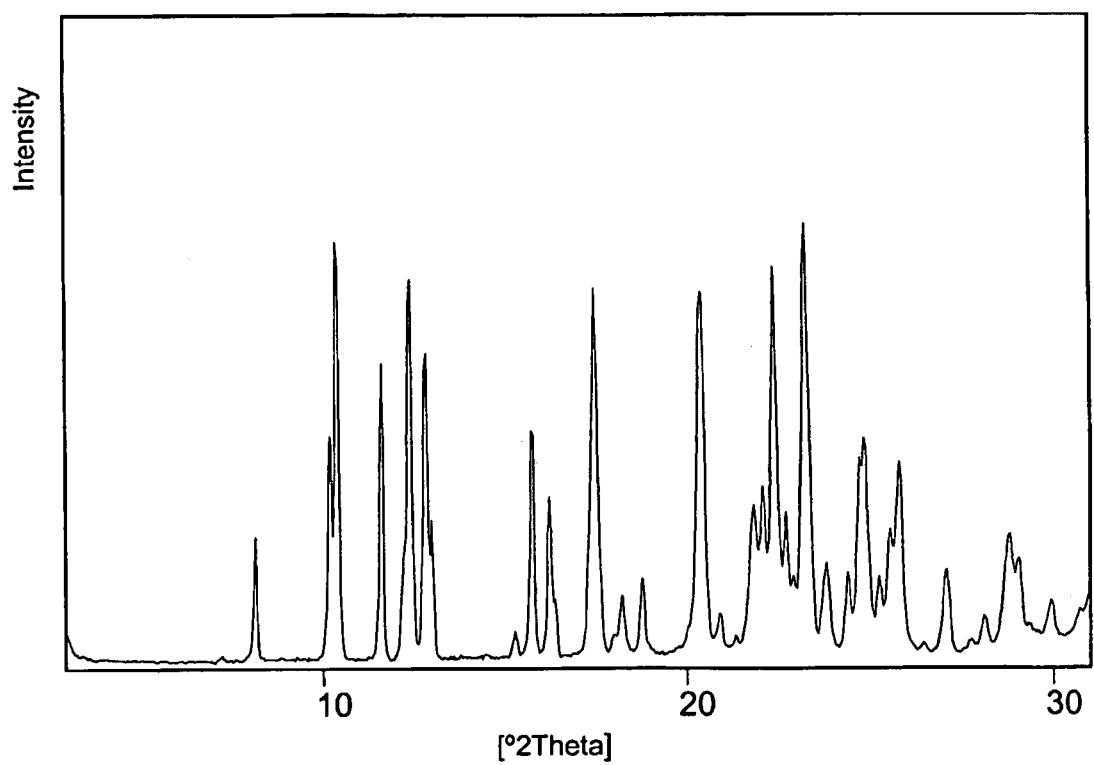
FIG. 2 represents X-ray powder diffractogram of crystal anhydrous hydrochloride salt of irbesartan.
Figure 3:
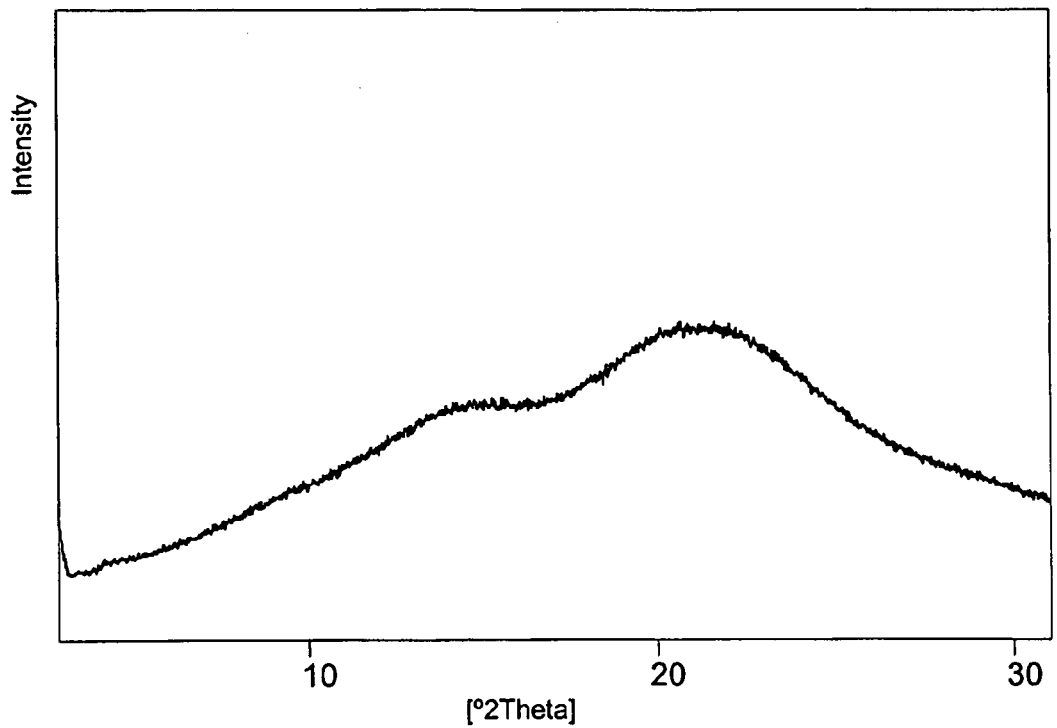
FIG. 3 represents X-ray powder diffractogram of amorphous anhydrous hydrochloride salt of irbesartan.

The present invention relates to a new and well-defined hydrate form of irbesartan hydrochloride, which is characterized by X-ray powder diffractogram and infrared spectrum and contains 3 molecules of water and 2 molecules of hydrochloride to 2 molecules of irbesartan. The sesquihydrate hydrochloride salt of irbesartan is prepared from aqueous suspensions or solutions of irbesartan with a pH-value below 1.2, preferably with a pH-value in the range between 1.0 and 0.5. By slowly heating the sesquihydrate hydrochloride salt of irbesartan in two steps, first to a temperature of about 120° C. and thereafter to a temperature from about 120° C. to about 160° C., a crystal anhydrous hydrochloride salt of irbesartan is formed. The duration of entire heating is more than 1 hour, preferably more than 3 hours. By a rapid heating of the sesquihydrate hydrochloride salt of irbesartan, which lasts less than 1 hour, preferably less than 20 minutes, an amorphous form of an anhydrous hydrochloride salt of irbesartan is formed.

Irbesartan used as the starting material may be in any form, e.g. it may be in a reaction solution, in crude form, in a filtrate, in an anhydrous, solvated or hydrated from, in an amorphous form or in any known crystal form or in the form of a mixture thereof.

Surprisingly, we have found that from an aqueous suspension or solution acidified to the pH-value below 1.2, a sesquihydrate hydrochloride salt of irbesartan is precipitated. By the preparation of this salt the inconvenient electrostaticity of irbesartan is avoided in an economic and easy manner suitable for the use in the work on an industrial scale, the new form is very stable in it does not decompose even at a longer heating at increased temperatures.

In the continuation the preferred embodiments of the process are described.

DETAILED DESCRIPTION OF THE INVENTION

The present invention relates to a new and well-defined sesquihydrate form of irbesartan hydrochloride characterized by X-ray powder diffractogram and infrared spectrum, which contains 3 molecules of water and 2 molecules of hydrochloride to 2 molecules of irbesartan. The sesquihydrate of irbesartan hydrochloride is prepared from aqueous suspensions or solutions of irbesartan, which are acidified to a pH-value below 1.2, preferably to a pH-value in a range between 1.0 and 0.5.

The invention also relates to an anhydrous hydrochloride salt of irbesartan, which is prepared by slowly heating the sesquihydrate form of irbesartan hydrochloride salt in two steps, first to a temperature of about 120° C. and then to a temperature from about 120° C. to about 160° C. By a rapid heating of sesquihydrate hydrochloride salt of irbesartan, which lasts less than 1 hour, preferably less than 20 minutes, an amorphous form of anhydrous hydrochloride salt of irbesartan is formed.

X-ray powder diffractograms were recorded with diffractometer Phillips PW 3040/60 X'Pert PRO; $CuK_\alpha$ radiation 0.1541874 nm.

The following abbreviations "S" and "m", which are used in the present application, mean: "s" relates to a strong relative intensity from 30% to 100% and "m" relates to a medium relative intensity from 10% to 30%.

The sesquihydrate form of 2-butyl-1-[2'-(1H-tetrazol-5-yl)bifenyl-4-yl-methyl]spiro[2-imidazoline-4.1'-cyclopentane]-5-one hydrochloride is characterized by the following data:

Characteristic X-ray powder diffractogram is represented by the following 2-theta values together with intensity designations:

TABLE 1

| [°2Th.] | intensity designation |
|---|---|
| 6.98 | m |
| 7.47 | m |
| 8.24 | s |
| 11.01 | s |
| 12.87 | s |
| 13.18 | s |
| 13.97 | s |
| 14.81 | s |
| 14.96 | s |
| 15.33 | s |
| 16.30 | s |
| 17.39 | s |
| 17.78 | s |
| 18.30 | m |
| 19.06 | m |
| 20.06 | s |
| 21.02 | s |
| 21.57 | m |
| 22.12 | s |
| 22.53 | s |
| 22.94 | s |
| 23.39 | s |
| 23.59 | s |
| 24.67 | m |
| 26.54 | s |
| 26.97 | s |
| 27.52 | m |
| 28.47 | m |
| 28.90 | m |
| 29.43 | m |

The sesquihydrate form of 2-butyl-1-[2'-(1H-tetrazol-5-yl)bifenyl-4-yl-methyl]spiro[2-imidazoline-4.1'-cyclopentane]-5-one hydrochloride is preferably characterized by the following 2-theta values: 7.47, 8.24, 11.01, 15.33, 17.39, 22.53, 23.39, 26.54.

The anhydrous crystal form of 2-butyl-1-[2'-(1H-tetrazol-5-yl)bifenyl-4-yl-methyl]spiro[2-imidazoline-4.1'-cyclopentane]-5-one hydrochloride is characterized by the following data:

Characteristic X-ray powder diffractogram is represented by the following 2-theta values together with intensity designations:

TABLE 2

| [°2Th.] | intensity designation |
|---|---|
| 8.16 | m |
| 10.20 | s |
| 10.39 | s |
| 11.61 | s |
| 12.38 | s |
| 12.81 | s |
| 13.00 | s |
| 15.74 | s |
| 16.23 | s |
| 17.48 | s |
| 18.22 | m |
| 18.78 | m |
| 20.40 | s |
| 21.83 | s |
| 22.08 | s |
| 22.38 | s |
| 22.71 | s |
| 23.22 | s |
| 23.79 | m |

TABLE 2-continued

| [°2Th.] | intensity designation |
|---|---|
| 24.38 | m |
| 24.69 | s |
| 24.84 | m |
| 25.25 | m |
| 25.55 | m |
| 25.79 | s |
| 27.07 | m |
| 28.78 | m |
| 29.03 | m |

The anhydrous form of 2-butyl-1-[2'-(1H-tetrazol-5-yl)bifenyl-4-yl-methyl]spiro[2-imidazoline-4.1'-cyclopentane]-5-one hydrochloride is preferably characterized by the following 2-theta values: 10.39, 11.61, 12.38, 12.81, 15.74, 17.48, 20.40, 21.83, 22.08, 22.38, 23.22 and 25.79.

IR-spectra were recorded on PERKIN ELMER FT-IR Spectrometer SPECTRUM 1000.

The irbesartan used as a starting material for the preparation of the described sesquihydrate hydrochloride salt of irbesartan and anhydrous forms of irbesartan hydrochloride salt may be in any form, e.g. it may be used when it is contained in a reaction solution, in a raw form, in a filtrate containing several solvents, or in an anhydrous or any solvated or hydrated form, in an amorphous or any of known crystal forms or in a mixture thereof.

Sesquihydrate hydrochloride salt of irbesartan and anhydrous forms of irbesartan hydrochloride salt prepared and described according to the present invention can also be used for the preparation of other polymorphous or amorphous forms of irbesartan or their mixtures.

Irbesartan of any known form or its salt is suspended or dissolved in water in any ratio, preferably in a ratio from 1:5 to 1:15 (w:w). The process can be carried out at temperatures between 0° C. and reflux temperature, preferably at room temperature.

In order to obtain more homogeneous suspensions, there can be added compounds decreasing the surface tension, preferably auxiliary solvents such as alcohols or other water-soluble organic solvents, preferably in amounts not exceeding 10% of the total volume.

The suspension or solution of irbesartan is acidified to a pH value below 1.2, preferably to a pH-value in the range between 1.0 and 0.5, with HCl, preferably in the form of its water solution. The concentration of hydrochloric acid must be sufficiently high to obtain such a pH. At the above-mentioned pH the suspension is stirred, preferably up to 5 hours at a temperature from 0° C. to 50° C., preferably at room temperature. The filtered-off product is dried in vacuum for 1 to 5 hours at a temperature between 50° C. and room temperature.

The product isolated is sesquihydrate of irbesartan hydrochloride salt. The amount of water that can be bound to a molecule of irbesartan may be from 5.5% to 7.0%, preferably from 6.2% to 6.4% of water.

By a slow heating of the sesquihydrate hydrochloride salt of irbesartan in two steps, first to a temperature about 120° C. and then to a temperature from about 120° C. to about 160° C., an anhydrous hydrochloride salt of irbesartan is formed. The entire heating lasts more than 1 hour, preferably more than 3 hours. By a rapid heating of sesquihydrate hydrochloride salt of irbesartan, which lasts less than 1 hour, preferably less than 20 minutes, an amorphous form of anhydrous hydrochloride salt of irbesartan is formed.

In both manners of heating or drying the amount of water in the sample gradually decreases from the starting amount (up to 7%) to the final anhydrous state of irbesartan hydrochloride. Therefore it is also possible to isolate samples of irbesartan hydrochloride with any content of water between 0% and 7%.

Sesquihydrate hydrochloride salt and anhydrous hydrochloride salts of irbesartan, which are objects of the present invention, can be used for the preparation of pharmaceutical compositions together with pharmaceutically acceptable carriers, diluents, excipients, additives, fillers, lubricants, binders, stabilisers, solvents or solvates.

The pharmaceutical composition can be in the form of tablets, capsules, pastilles, powder, syrup, solution, suspension, ointment or dragees and similar and can contain artificial flavourings, sweeteners and similar, in suitable solid or fluid carriers or diluents or in sterile media for the preparation of injection solutions or suspensions.

The present invention is illustrated by the following Examples, which do not limit the scope of the invention.

Example 1

Irbesartan (1.5 g) was suspended in water (15 mL) at room temperature and methanol (1.5 mL) was added thereto. Subsequently, the suspension was acidified with 1 M HCl to the pH 0.8, wherefore 6.8 mL of this solution were used. The suspension was stirred for 2 hours at room temperature, whereafter the precipitate was filtered off. The product was dried in a vacuum dryer at 50° C. for 1 hour and sesquihydrate hydrochloride salt of irbesartan (1.58 g) was isolated.

IR (characteristic peaks): 1760, 1639, 1513, 1323, 943, 741 $cm^{-1}$.

NMR: corresponds to irbesartan

Water (KF) 6.25%

Elemental analysis for sesquihydrate hydrochloride salt of irbesartan:

Calculated for irbesartan*HCl*1.5 $H_2O$:

61.03% C, 6.56% H, 17.08% N

Found:

60.79% C, 6.70% H, 17.02% N

Example 2

Sesquihydrate hydrochloride salt of irbesartan (3.25 g) was slowly heated to 120° C. in a flask under bubbling with nitrogen. It was heated for three hours. Subsequently, the heating was continued up to 160° C. for 1.5 hours. When this temperature was achieved, the heating was stopped and the precipitate was cooled.

An anhydrous crystal hydrochloride salt of irbesartan was isolated.

IR (characteristic peaks): 1774, 1627, 1518, 1329, 1070, 756 $cm^{-1}$.

NMR: corresponds to irbesartan

Elemental analysis for hydrochloride salt of irbesartan:

Calculated for irbesartan*HCl:

64.58% C, 6.29% H, 18.07% N

Found:

64.27% C, 6.38% H, 17.96% N

Example 3

During bubbling with argon the flask was heated on an oily bath to 160° C. Then irbesartan HCl*1½ water (3 g) was added thereto and it was gently stirred for 15 minutes. The substance dissolved and the melt was slowly cooled to room temperature until it solidified. The product was crushed and amorphous anhydrous irbesartan HCl was isolated.

T=120-147° C.

IR (characteristic peaks): 1773, 1627, 1509, 1321, 1065, 758 cm$^{-1}$.

NMR: corresponds to irbesartan

The invention claimed is:

1. A sesquihydrate hydrochloride salt of irbesartan, having 2 molecules of hydrochloride and 3 molecules of water to 2 molecules of irbesartan.

2. The sesquihydrate hydrochloride salt of irbesartan according to claim 1, exhibiting an X-ray powder diffractogram of FIG. 1.

3. The sesquihydrate hydrochloride salt of irbesartan according to claim 1, exhibiting the following 2-theta values in an X-ray powder diffractogram: 6.98, 7.47, 8.24, 11.01, 12.87, 13.18, 13.97, 14.81, 14.96, 15.33, 16.30, 17.39, 17.78, 18.30, 19.06, 20.06, 21.02, 21.57, 22.12, 22.53, 22.94, 23.39, 23.59, 24.67, 26.54, 26.97, 27.52, 28.47, 28.90, and 29.43.

4. The sesquihydrate hydrochloride salt of irbesartan according to claim 1, exhibiting the following 2-theta values: 7.47, 8.24, 11.01, 15.33, 17.39, 22.53, 23.39, and 26.54.

5. The sesquihydrate hydrochloride salt of irbesartan according to claim 1, exhibiting peaks in an IR spectrum at 1760, 1639, 1513, 1323, 943, 741 cm.sup.-1.

6. The sesquihydrate hydrochloride salt of irbesartan according to claim 1, containing from 5.5% to 7.0% of water.

7. A pharmaceutical composition comprising a sesquihydrate hydrochloride salt of irbesartan having 2 molecules of hydrochloride and 3 molecules of water to two molecules of irbesartan and pharmaceutically acceptable carriers, diluents, excipients, additives, fillers, lubricants, binders, stabilisers, or solvents.

8. The pharmaceutical composition according to claim 7, in the form of tablets, capsules, pastilles, powder, syrup, solution, suspension, ointment or dragees.

* * * * *